US00PP37837P2

(12) United States Plant Patent
Wagner et al.

(10) Patent No.: US PP37,837 P2
(45) Date of Patent: Nov. 3, 2026

(54) BLUEBERRY PLANT NAMED 'OBG-20010'

(50) Latin Name: *Vaccinium corymbosum*
Varietal Denomination: OBG-20010

(71) Applicant: Robert Gabriel, Silverton, OR (US)

(72) Inventors: Adam L. Wagner, Brownsville, OR (US); D. Scott NeSmith, Molena, GA (US)

(73) Assignee: Robert Gabriel, Silverton, OR (US)

( * ) Notice: Subject to any disclaimer, the term of this patent is extended or adjusted under 35 U.S.C. 154(b) by 0 days.

(21) Appl. No.: 19/536,698

(22) Filed: Feb. 11, 2026

(51) Int. Cl.
*A01H 6/36* (2018.01)
*A01H 5/08* (2018.01)

(52) U.S. Cl.
USPC ..... Plt./157

(58) Field of Classification Search
USPC ..... Plt./157
CPC ..... A01H 6/36; A01H 5/08
See application file for complete search history.

*Primary Examiner* — Keith O. Robinson
(74) *Attorney, Agent, or Firm* — Klarquist Sparkman, LLP

(57) ABSTRACT

A new and distinct blueberry plant variety named 'OBG-20010' is disclosed, characterized by its high yield, large and firm fruit, good texture and flavor, and good shelf life.

3 Drawing Sheets

Specification includes a Sequence Listing.

Latin name of the genus and species: *Vaccinium corymbosum.*

Variety denomination: 'OBG-20010'.

INCORPORATION OF ELECTRONIC SEQUENCE LISTING

The Sequence Listing is submitted as an XML file named "Sequence.xml," created on Jan. 12, 2026 (16,458 bytes), which is incorporated herein by reference.

BACKGROUND

The present disclosure relates to a new and distinct variety of highbush blueberry, or *Vaccinium corymbosum*, named 'OBG-20010'. *Vaccinium corymbosum* is of the family Ericaceae. The new *Vaccinium corymbosum* 'OBG-20010' was first identified in a cultivated area in Keizer, Oregon, USA.

SUMMARY

'OBG-20010' originated from seeds collected from open pollinated fruit of *Vaccinium corymbosum* 'TH-1009' (unpatented). The open-pollinated fruit was harvested from selection trial plots in 2020. The new variety is early mid-season, has large berries, and good flavor with no observed notable diseases or other pest problems beyond those also common for other varieties, and a chilling requirement of approximately 300-400 hours below 45° F.

The new blueberry plant variety 'OBG-20010' has been tested in asexually propagated (by vegetative cuttings) planting in Keizer, Oregon, USA, where it was also established for testing and comparison to industry standards. Asexual reproduction of this new variety by vegetative cuttings shows that the foregoing characteristics come true to form, are firmly fixed, and are established and transmitted through succeeding propagations.

The following traits have been repeatedly observed and are determined to be the unique and distinguishing characteristics of 'OBG-20010'. In combination, these traits set the new variety apart from all other existing varieties of highbush blueberry:

1. High yield (8.16 kg/plant)
2. Large fruit (21.8 mm, 5.0 g)
3. Firm fruit (339.0 g/mm$^3$)
4. Good shelf life (>4 weeks)
5. Good texture and flavor In trials that were performed in Brooks, Oregon, USA, standards 'FL06-203' (Avanti™, U.S. Plant Pat. No. 26,312), 'Biloxi' (unpatented) and 'Suziblue' (U.S. Plant Pat. No. 21,167) were chosen for comparison as the most similar commercially available varieties.

'Biloxi' was introduced in 1998 by the USDA's Agricultural Research Service at Mississippi State University. While the variety was widely planted, many 'Biloxi' growers today are actively seeking a replacement due to its small berry size and less appealing flavor profile. The 'Suziblue' variety was introduced to the market in 2009 and remains popular due to its combination of vigor, acceptable berry size and acceptable firmness. 'FLO6-203' was developed at the University of Florida and introduced to the market in 2015. It has had limited success outside of Florida due to its smaller berry and modest yield. 'OBG-20010' represents an advancement over all standards as measured by berry weight, size, firmness and yield. Table 1 below compares 'OBG-20010' to 'FLO6-203', 'Biloxi' and 'Suziblue'.

TABLE 1

Comparison of 'OBG-20010' to three commercial varieties

| | 'OBG-20010' | 'Biloxi' | 'Suziblue' | 'Fl06-203' |
|---|---|---|---|---|
| Avg. Berry Weight | 5.00 | 2.21 | 3.48 | 2.77 |

TABLE 1-continued

Comparison of 'OBG-20010' to three commercial varieties

| | 'OBG-20010' | 'Biloxi' | 'Suziblue' | 'Fl06-203' |
|---|---|---|---|---|
| Avg. Berry Diameter (mm) | 21.80 | 15.80 | 19.47 | 16.92 |
| Berry Firmness ($g/mm^3$) Over 4 Weeks | 339.00 | 249.83 | 285.47 | 244.41 |
| Titratable Acidity (% CA) | 2.1 | 3.0 | 2.0 | 3.0 |
| Avg. Soluble Solids (%) | 10.2 | 17.6 | 13.6 | 13.1 |
| Avg. pH | 3.80 | 3.70 | 3.93 | 3.60 |
| Yield per Mature Plant (kg) | 8.16 | 3* | 1.4* | 4 |
| Berry Quality After 4 Weeks** | 5 | 3 | 3 | 4 |

*Yield measures were uncharacteristically low in the data year. 3-year average was 5.15 kg for 'Biloxi' and 3.9 kg for 'Suziblue'.
**Subjective measure on 1-5 scale (5 best)

The key improvements 'OBG-20010' offers to consumers include:

Large berry size and weight

Firm fruit

Good shelf life

'OBG-20010' is an exceptional and unique new variety that will benefit the commercial blueberry industry. The plant can be machine harvested and the fruit quality is acceptable for the fresh, frozen or pureed blueberry markets.

BRIEF DESCRIPTION OF THE PHOTOGRAPHS

Figure 1:
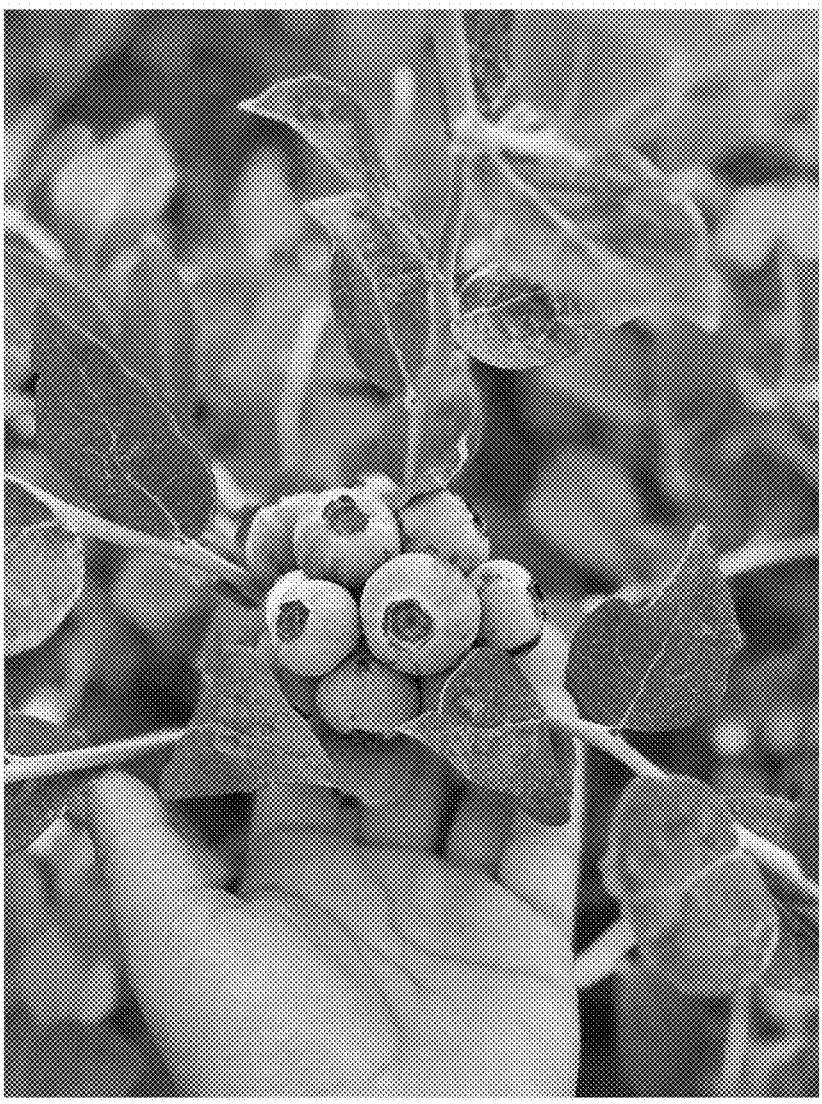
FIG. 1 is a photograph showing a close-up of 'OBG-20010' fruit taken under natural outdoor light conditions in July 2025.
Figure 2:
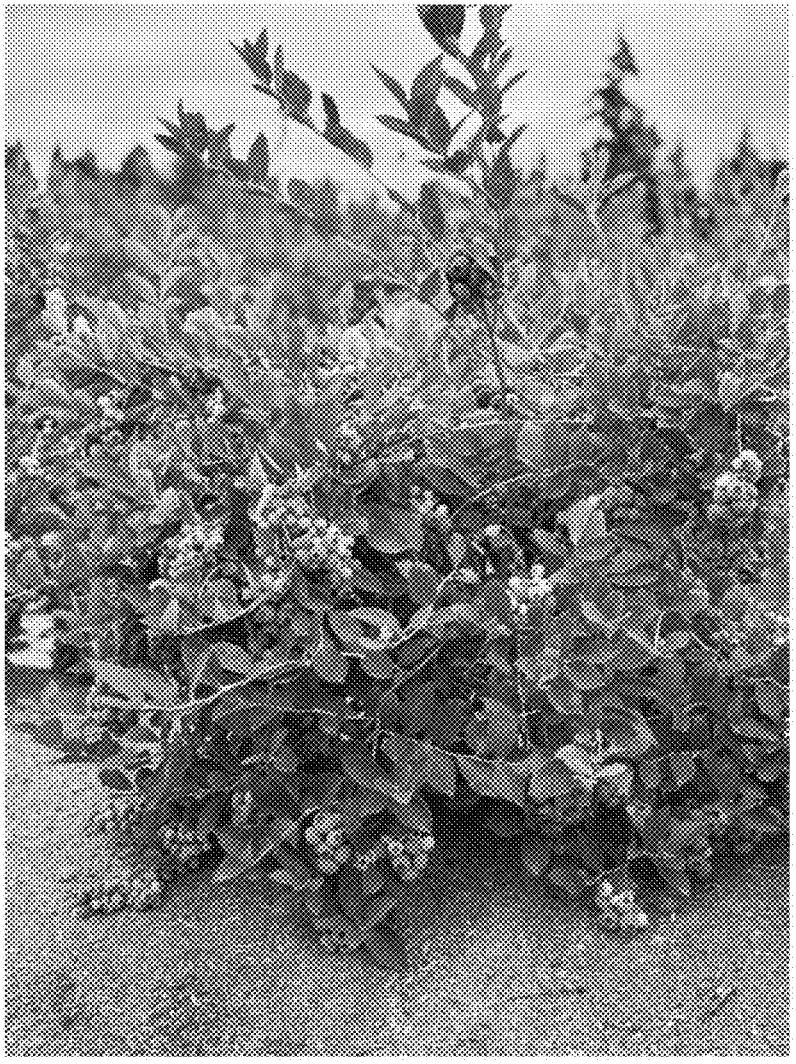
FIG. 2 is a photograph of 'OBG-20010' fruit on a 4-year-old plant. The photograph was taken under natural outdoor light conditions in July 2025.
Figure 3:
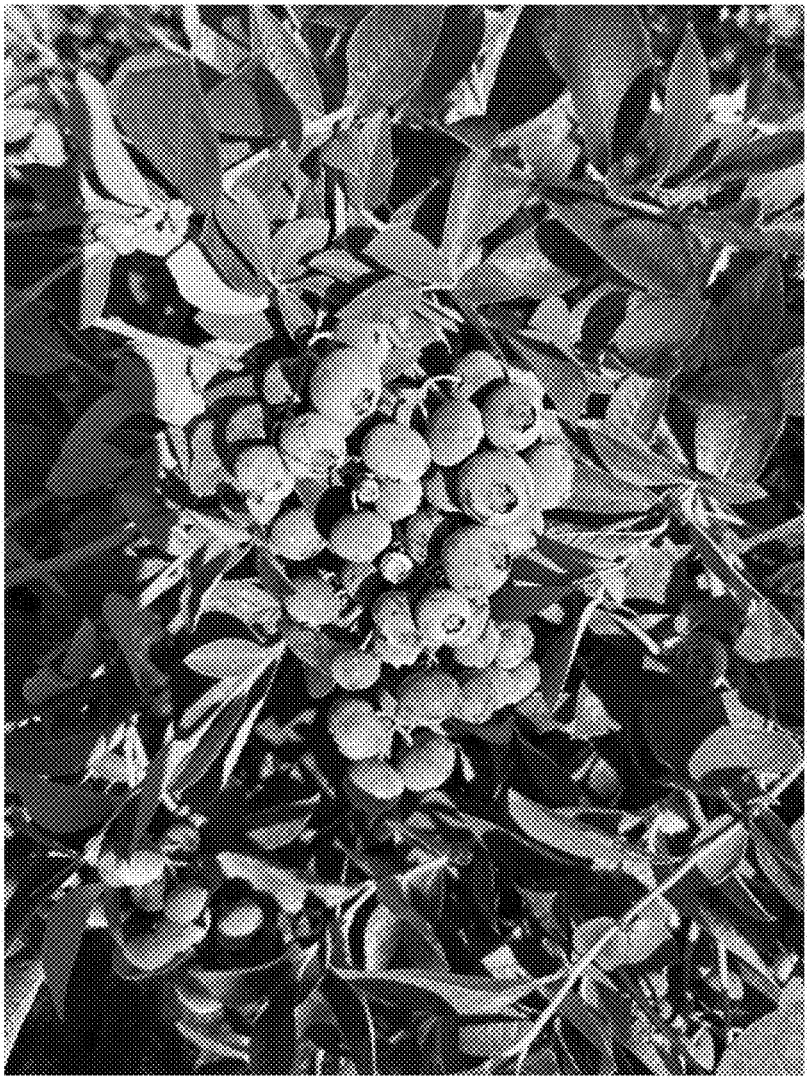
FIG. 3 is a photograph of an 'OBG-20010' fruit cluster on a four year-old plant. The photograph was taken under natural outdoor light conditions in July 2025.

The color photographs show typical specimens of the new variety and depict the color as nearly true as is reasonably possible to make the same in a color illustration of this character. It should be noted that colors may vary, for example due to lighting conditions at the time the photograph is taken. Therefore, color characteristics of this new variety should be determined with reference to the observations described herein, rather than from the photograph alone.

DETAILED DESCRIPTION

Color descriptions and other terminology in this application are used in accordance with their ordinary dictionary descriptions, unless the context clearly indicates otherwise. Color designations (hue/value/chroma) are made with reference to The Royal Horticultural Society Colour Chart (R.H.S.), $5^{th}$ edition, London, England, 2007.

The following detailed description of 'OBG-20010' is based on observations of asexually reproduced progeny six years of age. The following detailed description concerns plants growing in open fields with supplemental irrigation in Keizer, Oregon, USA. The average low temperature for the year ranges from 40-45° F., and the average high temperature of the year ranges from 90-95° F. The color values were determined in the 2025 growing season under natural light conditions in Keizer, Oregon, USA.

'OBG-20010' has not been observed under all environmental conditions. Certain phenotypic characteristics of this variety may change with changing environmental conditions such as photoperiod, temperature, moisture, soil conditions, nutrient availability, or other factors without any variance in genotype.

Botanical classification: *Vaccinium corymbosum.*

Common name: Highbush blueberry.

Commercial classification: Fruit-bearing shrub.

Parentage:

*Female parent.*—'TH-1009' (unpatented).

*Male parent.*—Unknown.

Plant:

*Average height.*—86 cm.

*Average canopy diameter.*—84 cm. Growth Habit: Bushy, Short, Compact. Suckering: Moderate-low.

*Productivity.*—3 Years Old: 10 lbs/plant. 4 Years Old: 18 lbs/plant.

*Degree of vigor.*—Moderate.

*Plant hardiness zone.*—USDA 7B-9B.

*Suitability for mechanical harvesting.*—Good.

Deciduousness:

*Foliage retention.*—Fully Deciduous.

*One-year old canes.*—Average Length: 41.75 cm. Average Diameter at Base: 4.9 cm. Average Diameter at Tip: 2.7 cm. Texture: Smooth, glaucous. Color: RHS 144C.

Foliage:

*Leaf color.*—Spring Color: Upper Surface: RHS 144A. Lower Surface: RHS 138B. Fall Color: Upper Surface: RHS 183B. Lower Surface: RHS 194C.

*Upper surface texture.*—Smooth, Glaucous.

*Lower surface texture.*—Smooth, Glaucous.

*Leaf arrangement.*—Alternate.

*Leaf shape.*—Elliptic.

*Leaf margin.*—Entire.

*Leaf venation.*—Reticulate.

*Leaf apices.*—Aristulate.

*Leaf bases.*—Cuneate.

*Leaf attitude.*—Ascending.

*Leaf dimensions.*—Length: 61.5 mm. Width: 35.3 mm.

*Leaf petiole.*—Average Length: 4.2 mm. Average Width: 1.5 mm. Color: RHS 141D. Surface Texture: Smooth.

Stem:

*Wood texture.*—New Wood (June/July): Smooth, Glaucous. 1 Year Wood (August): Smooth Glaucous. 3 Year Wood (August): Rough, Exfoliating.

*Wood color.*—New Wood (June/July): RHS 144B. 1 Year Wood (August): RHS 144C. 3 Year Wood (August): RHS 165A.

*Wood buds.*—Average Number of Flower Buds per Fruiting Lateral (in August): 8.

Inflorescence/flowers:

*Average flowering period.*—Late Match to Mid-April.

*Average time of beginning of flowering.*—Mid-March.

*Average time of* 50% *anthesis*.—Mid-April.
*Average time of beginning of leaf bud burst*.—Mid-to Late-April.
*Inflorescence size*.—Average Length: 150 mm. Average Width: 66 mm.
*Flowering cluster density*.—Moderate.
*Average number of flowers per peduncle*.—7.
*Self-compatibility*.—Moderately self-fertile but requires pollination from another highbush blueberry for maximum fruit development.
*Flower buds*.—Immature Bud Color: RHS NN155C. Mature Bud Color: RHS NN155C. Average Bud Length: 10.55 mm. Average Bud Width: 5.98 mm.
*Flower pedicel*.—Color: RHS N144C. Average Length: 13.4 mm. Texture: Smooth.
*Flower peduncle*.—Color: RHS N144C. Average Length: 26.6 mm.
*Individual flower*.—Fragrance: None. Flower Shape: Urceolate. Average Flower Length: 10.15 mm. Average Protrusion of Stigma Beyond Corolla: 0.7 mm.
*Calyx*.—Color: RHS 143A. Surface: Smooth. Average Diameter: 6.08 mm.
*Corolla*.—Color: RHS NN155C. Average Length: 8.91 mm. Average Width: 8.35 mm. Average Aperture/Width: 4.01 mm. Anthocyanin Coloration of Corolla at Time of Anthesis: Low to None. Corolla Ridges: Present.
*Stamen*.—Average Length: 6.7 mm. Number: 10.Filament Color: RHS 145D.
*Anther*.—Average Length: 4.38 mm. Average Number: 10. Color: RHS 164A.
*Pollen*.—Abundance: High. Color: RHS 158B.
*Pistil*.—Average Length: 9.9 mm. Ovary Color (exterior): RHS 138B. Average Style Length: 7.84 mm. Style Color: RHS 144C.

Fruit:
*Time of fruit ripening*.—Early May.
*Time of* 50% *maturity*.—Early June.
*Time of harvest*.—Late June.
*Fruit development period*.—60 days.
*Cluster density*.—Moderately High.
*Average berries per cluster*.—7.
*Unripe berry color*.—RHS 142D.
*Unripe skin color after polishing*.—RHS 145B.
*Ripe berry color*.—RHS 101C.
*Ripe berry skin color after polishing*.—RHS N186A.
*Berry surface wax abundance*.—High.
*Berry flesh color*.—RHS 158D.
*Average berry height*.—5.0 g.
*Average berry height from calyx to scar*.—17.86 mm.
*Average berry diameter*.—21.8 mm.
*Average calyx aperture*.—9.59 mm.
*Average calyx depth*.—2.7 mm.
*Average pedicel length*.—16.18 mm.
*Pedicel surface texture*.—Smooth, glaucous.
*Berry attachment force*.—Moderate.
*Berry shape*.—Oblate.
*Fruit stem scar*.—Moderate Large.
*Berry flavor*.—High.
*Average berry sweetness when ripe*.—10.2% Soluble Solids.
*Average berry firmness when ripe*.—339.0 g/mm$^3$.
*Berry shelf life*.—Exceeds 4 weeks.

Seed:
*Seed color*.—RHS N167B.
*Average seed length*.—1.75 mm.
*Average seed width*.—1.08 mm.
*Average seed dry weight*.—0.44 mg.
*Average quantity seeds per berry*.—35.

Disease/pest resistance/susceptibility:
*Root rot* (*Phytophthora cinnamomic*).—Does not appear to be overly susceptible.
*Stem blight* (*Botryosphaeria spp.*).—Undetermined.
*Phomopsis twig blight* (*Phomopsis vaccinii*).—Does not appear to be overly susceptible.
*Botryosphaeria stem canker* (*Botryosphaeria corticis*).—Does not appear to be overly susceptible.
*Bacterial cane canker* (*Pseudomonas syringae*).—Does not appear to be overly susceptible.
*Botrytis blight* (*Botrytis cinerea*).—Does not appear to be overly susceptible.
*Leaf spot* (*Septoria spp.*).—Does not appear to be overly susceptible.
*Leaf rust* (*Naohidemyces vaccinii*).—Does not appear to be overly susceptible.
*Bud mites* (*Acalitus vaccinii*).—Undetermined.

Primary market use: Fresh, frozen and pureed fruit markets.

Genetic Fingerprinting

2×4 mm leaf tissue punches were pooled together into a 2 ml tube. 1 cubic zirconia bead and 100 ul PVP lysis buffer was added. The sample was ground at 1400 RPM for 1 minute, after which 250 μl of additional PVP lysis buffer was added. The sample was incubated at 60° C. for 1 hour and DNA was extracted following AutoGenepure® speed extraction protocol. Nine microsatellite markers (Marker 1-Marker 9) were then assayed by PCR reaction on the extracted DNA. The PCR product was diluted into a running buffer and subject to electrophoresis. Analysis was done using GeneMarker® software.

Variety differentiation is based on the amplified peaks of individual markers, which depend on the genetic makeup of the variety (See, e.g., Boches et al. "Genetic Diversity in the Highbush Blueberry Evaluated with Microsatellite Markers" *J. Amer. Soc. Hort. Sci.* 131(5):674-686, 2006). Each variety displays different peak patterns for each marker, creating a unique genetic "fingerprint." The unique genetic fingerprint for 'OBG-20010' is:

Marker 1: 290, 296
Marker 2: 189, 195
Marker 3: 221, 229
Marker 4: 189, 194
Marker 5: 113, 116
Marker 6: 238, 244, 254
Marker 7: 374, 380
Marker 8: 313, 319, 324, 332
Marker 9:

TABLE 2

Primer pairs for marker detection.

| Marker # | Forward | Reverse |
|---|---|---|
| 1 | TCCTCGTTCTCTCCCTCTCA (SEQ ID NO: 1) | CGCTGAAGTTGGAGTCCTT (SEQ ID NO: 2) |
| 2 | TCAGACATGATTGGGGAGGT (SEQ ID NO: 3) | GGAATAATAGAGGCGGTGGA (SEQ ID NO: 4) |
| 3 | GTTAAGCTTTTAGATGAGTTG ATGG (SEQ ID NO: 5) | AACCAGTCCCAGACCCAAAT (SEQ ID NO: 6) |

TABLE 2-continued

Primer pairs for marker detection.

| Marker # | Forward | Reverse |
|---|---|---|
| 4 | CGCAATCGCTGCATAGTTTA (SEQ ID NO: 7) | GTTTAACGTTGCAACCAATTC CA(SEQ ID NO: 8) |
| 5 | TAGTGGAGGGTTTTGCTTGG (SEQ ID NO: 9) | ATCGAAGCGAAGGTCAAAGA (SEQ ID NO: 10) |
| 6 | CGCGTGAAAAACGACCTAAT (SEQ ID NO: 11) | ACTCGATCCCTCCACCTG (SEQ ID NO: 12) |

TABLE 2-continued

Primer pairs for marker detection.

| Marker # | Forward | Reverse |
|---|---|---|
| 7 | CACCCATTTCACGGAATCTC (SEQ ID NO: 13) | ACTTGGTCGGGTGTTGTCTC (SEQ ID NO: 14) |
| 8 | TCTCTTTCCCTTTTCAAGTGG (SEQ ID NO: 15) | GTTTATGATGGAATTCCGAGTT TG (SEQ ID NO: 16) |
| 9 | GTTCATCCCAATGCAGAAGA AG (SEQ ID NO: 17) | GTTTCCTCTTGTGGGTTAGGG TTTCT (SEQ ID NO: 18) |

SEQUENCE LISTING

```
Sequence total quantity: 18
SEQ ID NO: 1            moltype = DNA  length = 20
FEATURE                 Location/Qualifiers
source                  1..20
                        mol_type = other DNA
                        organism = synthetic construct
SEQUENCE: 1
tcctcgttct ctccctctca                                                20

SEQ ID NO: 2            moltype = DNA  length = 19
FEATURE                 Location/Qualifiers
source                  1..19
                        mol_type = other DNA
                        organism = synthetic construct
SEQUENCE: 2
cgctgaagtt ggagtcctt                                                 19

SEQ ID NO: 3            moltype = DNA  length = 20
FEATURE                 Location/Qualifiers
source                  1..20
                        mol_type = other DNA
                        organism = synthetic construct
SEQUENCE: 3
tcagacatga ttggggaggt                                                20

SEQ ID NO: 4            moltype = DNA  length = 20
FEATURE                 Location/Qualifiers
source                  1..20
                        mol_type = other DNA
                        organism = synthetic construct
SEQUENCE: 4
ggaataatag aggcggtgga                                                20

SEQ ID NO: 5            moltype = DNA  length = 25
FEATURE                 Location/Qualifiers
source                  1..25
                        mol_type = other DNA
                        organism = synthetic construct
SEQUENCE: 5
gttaagcttt tagatgagtt gatgg                                          25

SEQ ID NO: 6            moltype = DNA  length = 20
FEATURE                 Location/Qualifiers
source                  1..20
                        mol_type = other DNA
                        organism = synthetic construct
SEQUENCE: 6
aaccagtccc agacccaaat                                                20

SEQ ID NO: 7            moltype = DNA  length = 20
FEATURE                 Location/Qualifiers
source                  1..20
                        mol_type = other DNA
                        organism = synthetic construct
SEQUENCE: 7
cgcaatcgct gcatagttta                                                20

SEQ ID NO: 8            moltype = DNA  length = 23
FEATURE                 Location/Qualifiers
source                  1..23
```

-continued

```
                        mol_type = other DNA
                        organism = synthetic construct
SEQUENCE: 8
gtttaacgtt gcaaccaatt cca                                          23

SEQ ID NO: 9            moltype = DNA  length = 20
FEATURE                 Location/Qualifiers
source                  1..20
                        mol_type = other DNA
                        organism = synthetic construct
SEQUENCE: 9
tagtggaggg ttttgcttgg                                              20

SEQ ID NO: 10           moltype = DNA  length = 20
FEATURE                 Location/Qualifiers
source                  1..20
                        mol_type = other DNA
                        organism = synthetic construct
SEQUENCE: 10
atcgaagcga aggtcaaaga                                              20

SEQ ID NO: 11           moltype = DNA  length = 20
FEATURE                 Location/Qualifiers
source                  1..20
                        mol_type = other DNA
                        organism = synthetic construct
SEQUENCE: 11
cgcgtgaaaa acgacctaat                                              20

SEQ ID NO: 12           moltype = DNA  length = 18
FEATURE                 Location/Qualifiers
source                  1..18
                        mol_type = other DNA
                        organism = synthetic construct
SEQUENCE: 12
actcgatccc tccacctg                                                18

SEQ ID NO: 13           moltype = DNA  length = 20
FEATURE                 Location/Qualifiers
source                  1..20
                        mol_type = other DNA
                        organism = synthetic construct
SEQUENCE: 13
cacccatttc acggaatctc                                              20

SEQ ID NO: 14           moltype = DNA  length = 20
FEATURE                 Location/Qualifiers
source                  1..20
                        mol_type = other DNA
                        organism = synthetic construct
SEQUENCE: 14
acttggtcgg gtgttgtctc                                              20

SEQ ID NO: 15           moltype = DNA  length = 21
FEATURE                 Location/Qualifiers
source                  1..21
                        mol_type = other DNA
                        organism = synthetic construct
SEQUENCE: 15
tctctttccc ttttcaagtg g                                            21

SEQ ID NO: 16           moltype = DNA  length = 22
FEATURE                 Location/Qualifiers
source                  1..22
                        mol_type = other DNA
                        organism = synthetic construct
SEQUENCE: 16
gtttatgatg gaattccgag tt                                           22

SEQ ID NO: 17           moltype = DNA  length = 22
FEATURE                 Location/Qualifiers
source                  1..22
                        mol_type = other DNA
                        organism = synthetic construct
SEQUENCE: 17
gttcatccca atgcagaaga ag                                           22

SEQ ID NO: 18           moltype = DNA  length = 26
```

-continued

```
FEATURE                 Location/Qualifiers
source                  1..26
                        mol_type = other DNA
                        organism = synthetic construct
SEQUENCE: 18
gtttcctctt gtgggttagg gtttct                                          26
```

We claim:

1. A new and distinct variety of blueberry plant named 'OBG-20010', substantially as illustrated and described herein.

* * * * *